US00PP22132P2

(12) United States Plant Patent
Korlipara

(10) Patent No.: US PP22,132 P2
(45) Date of Patent: Sep. 6, 2011

(54) ***ECHINACEA* PLANT NAMED 'TNGD'**

(50) Latin Name: ***Echinacea* spp.**
Varietal Denomination: TNGD

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/800,255

(22) Filed: May 11, 2010

(51) Int. Cl.
*A01H 5/00* (2006.01)

(52) U.S. Cl. ..... Plt./428

(58) Field of Classification Search ..... Plt./428
See application file for complete search history.

*Primary Examiner* — June Hwu
(74) *Attorney, Agent, or Firm* — Klarquist Sparkman, LLP

(57) ABSTRACT

A new and distinct *Echinacea* plant named 'TNGD' characterized by dark pink ray florets, enlarged deep pink disc florets forming an anemone-type inflorescence, a tall habit with good branching and strong stems, and excellent vigor.

1 Drawing Sheet

Botanical denomination: *Echinacea* spp.
Variety designation: 'TNGD'.

The present invention relates to a new and distinct cultivar of *Echinacea* and given the cultivar name 'TNGD'. *Echinacea* is in the family Asteraceae. This new cultivar is a second generation seeding originating from a planned breeding program using *Echinacea purpurea* 'Razzmatazz' (U.S. Plant Pat. No. 13,894) as the seed parent in the original cross and unnamed proprietary, unreleased plant from a third generation hybrid of *Echinacea* (*paradoxa*×*purpurea* 'Ruby Giant'), for the pollen parent. The exact parents of this selection are unknown, unnamed, proprietary plants.

Compared to *Echinacea purpurea* 'Razzmatazz' (U.S. Plant Pat. No. 13,894), the seed parent in the original breeding line, the new variety has larger, darker pink inflorescences.

This new *Echinacea* cultivar is distinguished by:

1. dark pink ray florets,
2. enlarged deep pink disc florets forming an anemone-type inflorescence,
3. a tall habit with good branching and strong stems, and
4. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows the inflorescences of *Echinacea* 'TNGD' cut from a plant growing in the ground in full sun in the field in late summer in Canby, Oreg.

DETAILED PLANT DESCRIPTION

The following is a detailed description of the new *Echinacea* cultivar based on observations of an 18-month-old specimen growing in the ground in the garden in full sun under typical outdoor conditions in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, 5$^{th}$ edition.

Plant:

*Type.*—Herbaceous perennial.
*Hardiness.*—USDA Zones 4 to 9.
*Size.*—Grows to about 65 cm wide and 80 cm tall to top of inflorescences.
*Form.*—Basal clump, with 6 to 12 crowns.
*Vigor.*—Excellent.
*Roots.*—Fibrous, with many downward growing and few laterals, ivory in color, Yellow White 158D, roots develop easily from cuttings from the crown.

Stem (flowering):

*Type.*—Ascending, with 0 to 3 flowering branches on main stems.
*Size.*—Branching to 80 cm tall to a terminal inflorescence and 7 mm wide at base.
*Internode length.*—7 cm to 18 cm.
*Surface texture.*—Strigose.
*Color.*—Yellow Green N144A mottled Yellow Green 144A on the shaded side and tinted Greyed Orange 177A on the sunny side.

Leaf (basal):

*Type.*—Simple.
*Shape.*—Ovate to broadly lanceolate.
*Arrangement.*—Basal.
*Blade size.*—Grows to 14 cm long and 8 cm wide.
*Margins.*—Broadly serrate.
*Apex.*—Acute.
*Base.*—Attenuate.
*Surface texture.*—Strigose on both sides.
*Venation.*—Pinnate.
*Color.*—Topside, Green 137A, bottom side closest to Yellow Green 147B.
*Petiole description.*—Grows to 32.5 cm long and 4 mm wide, strigose along furrow, Yellow Green N144A except at base where Greyed Purple 187A.

Leaf (stem):

*Type.*—Simple.

*Shape.*—Broadly ovate to lanceolate.

*Arrangement.*—Alternate.

*Blade size.*—Grows to 9 cm long and 4.5 cm wide.

*Margins.*—Coarsely serrate.

*Apex.*—Acute.

*Base.*—Attenuate.

*Surface texture.*—Strigose on both sides.

*Venation.*—Pinnate.

*Color.*—Topside, Green 137A, bottom side closest to Yellow Green 147B.

*Petiole description.*—On lowermost leaves only, clasping, grows to 12 cm long and 4 mm wide above the clasp, strigose, Yellow Green 145A.

Inflorescence:

*Type.*—Composite on terminal stalked heads.

*Number of flowering stems from the ground.*—3 to 12.

*Flowering stem.*—Grows to 80 cm tall from the base of the plant to the terminal inflorescence and can grow to 18 cm long from the top stem leaf to the base of an inflorescence; branched, about 3 inflorescences per stem; diameter growing to 7 mm wide near the inflorescence; strigose, Yellow Green N144A mottled Yellow Green 144A.

*Size.*—Grows to 8.5 cm wide and 3 cm deep as disc enlarges.

*Form.*—Ray florets held slightly reflexed, mature disc is conic.

*Immature inflorescence.*—Grows to 3 cm wide and 2 cm deep, ray florets held slightly upright and rolled up so only the back color shows, Purple N77B, disc background is Yellow Green 145A, foreground is Brown N200A.

*Ray florets.*—Without pistil or stamen, about 21 in number, grows to 40 mm long and 12 mm wide, oblanceolate with the tip two toothed (each acute), entire margins, base attenuate, glabrous on both sides; topside color between Red Purple 70A and 70B on the top ⅔ and Red Purple 64B on the bottom ⅔, bottom side closest to Purple N77B.

*Disc.*—Flat becoming conic, becoming 25 mm deep and 48 mm wide with maturity, overall color is Red Purple 64A.

*Disc florets.*—About 200 in number, each with 1 pistil and 4 stamen, grow to 19 mm long and 6 mm wide, each with one persistent, very stiff bract (14 mm long with the top 3 mm colored Greyed Purple 187A on tip then Orange Red 32A, rest Yellow Green 148D); showy 3 to 4 lobed corollas to 17 mm long and 4 to 6 mm wide, tubular on the bottom with the lobes spread out like a fan, glabrous, back side color Red Purple 70B, inside color Red Purple 64A; pistil 8 mm long, ovary 2.5 mm long, White 155A, style 5 mm long Green White 157D, 2-branched stigma spreading 1.5 mm wide, Greyed Purple 187B; stamen 4.5 mm long, anthers 2.5 mm long and Greyed Purple N186A, filaments 2 mm long, White 155A, very little pollen, Orange 26B.

*Phyllaries.*—In 4 leafy series, area 3.5 cm wide and 12 mm deep, lobes lanceolate in shape, reflexed, grow to 12 mm long and 2.8 mm wide, Yellow Green 146A, margins strigose, tip acute, strigose on both sides.

*Receptacle.*—Grows to 10 mm wide and 17 mm deep, White 155A.

*Bloom period.*—July through October in Canby, Oreg.

*Fragrance.*—Light, floral.

*Lastingness.*—Each inflorescence lasts about two weeks in Canby, Oreg.

Seeds: 0 to 1 per inflorescence, each 3 mm long and 2.5 mm wide, oval, Brown 200C

*Fertility.*—Poor.

Disease and pests: *Echinacea* are susceptible to leaf miners, powdery mildew, bacterial spots, and gray mold. None of these have been observed on plants grown under commercial conditions in Canby, Oreg. No resistance is known.

I claim:

1. A new and distinct *Echinacea* plant as herein illustrated and described.

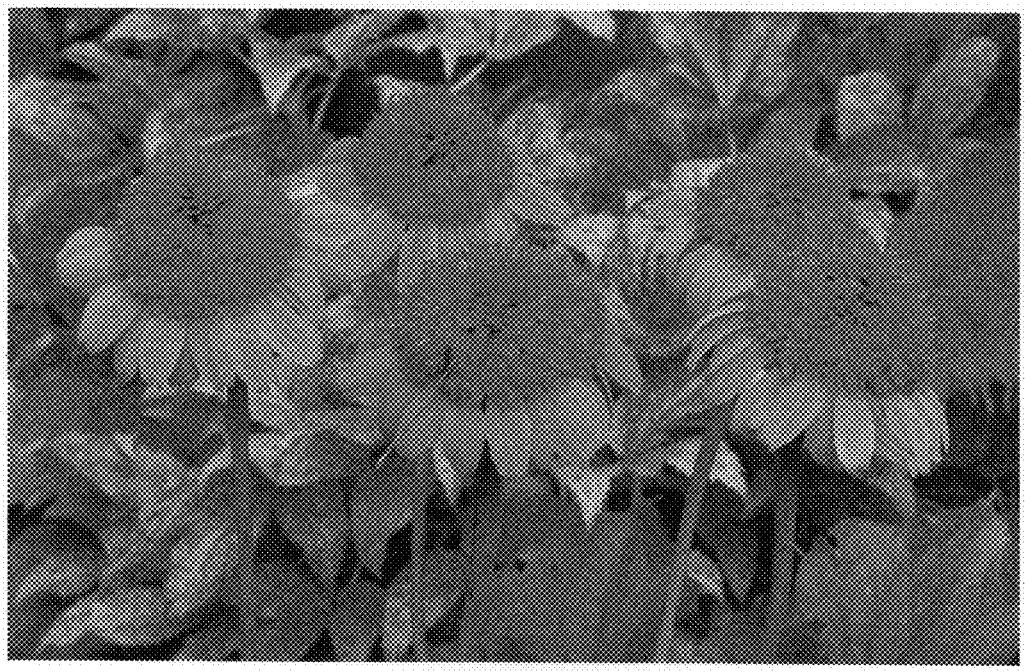

* * * * *